(12) United States Patent
Lecat

(10) Patent No.: US 8,257,089 B2
(45) Date of Patent: Sep. 4, 2012

(54) AUSCULTATION TRAINING DEVICE AND RELATED METHODS

(76) Inventor: Paul Jacques Charles Lecat, Tallmadge, OH (US)

( * ) Notice: Subject to any disclaimer, the term of this patent is extended or adjusted under 35 U.S.C. 154(b) by 311 days.

(21) Appl. No.: 12/206,131

(22) Filed: Sep. 8, 2008

(65) Prior Publication Data
US 2009/0117527 A1 May 7, 2009

Related U.S. Application Data

(63) Continuation of application No. 11/935,468, filed on Nov. 6, 2007.

(60) Provisional application No. 61/102,971, filed on Jan. 28, 2008.

(51) Int. Cl.
*G09B 11/00* (2006.01)

(52) U.S. Cl. ........................... 434/266; 434/262

(58) Field of Classification Search ............... 434/262, 434/266
See application file for complete search history.

(56) References Cited

U.S. PATENT DOCUMENTS

| | | | | |
|---|---|---|---|---|
| 3,665,087 | A * | 5/1972 | Poylo | 434/266 |
| 3,947,974 | A * | 4/1976 | Gordon et al. | 434/266 |
| 4,770,189 | A | 9/1988 | Shyu | |
| 6,220,866 | B1 * | 4/2001 | Amend et al. | 434/266 |
| 6,461,165 | B1 * | 10/2002 | Takashina et al. | 434/265 |
| 6,503,087 | B1 * | 1/2003 | Eggert et al. | 434/262 |
| 6,527,559 | B2 * | 3/2003 | Yoshii et al. | 434/266 |
| 6,758,676 | B2 * | 7/2004 | Eggert et al. | 434/262 |
| 7,115,102 | B2 * | 10/2006 | Abbruscato | 600/586 |
| 7,209,796 | B2 * | 4/2007 | McKinney et al. | 700/94 |
| 7,289,634 | B2 * | 10/2007 | Grove | 381/67 |
| 2003/0002685 | A1 | 1/2003 | Werblud | |
| 2004/0076303 | A1 * | 4/2004 | Vyshedskly et al. | 381/67 |
| 2004/0157612 | A1 * | 8/2004 | Kim, II | 455/445 |
| 2005/0048455 | A1 * | 3/2005 | Hayamizu et al. | 434/262 |
| 2005/0131307 | A1 | 6/2005 | Ruiter et al. | |
| 2005/0148283 | A1 | 7/2005 | Schwalm | |
| 2005/0181342 | A1 * | 8/2005 | Toly | 434/262 |
| 2006/0129067 | A1 | 6/2006 | Grajales et al. | |
| 2007/0117077 | A1 * | 5/2007 | Gordon et al. | 434/262 |
| 2007/0178430 | A1 | 8/2007 | Lecat | |

FOREIGN PATENT DOCUMENTS

JP 09-146452 6/1997

(Continued)

OTHER PUBLICATIONS

Technology to Inspire: Technology Archive Electronic Stethoscope, web page article, Feb. 2007, http://www.youngforesight.org/default.asp?section=Technology&chapter=CAT003.

International Preliminary Report on Patentability, dated Mar. 15, 2011, World Intellectual Property Organization, PCT/US2008/082417.

Supplementary European Search Report and Written Opinion, dated Jan. 27, 2011, European Patent Office, EP08847944.9.

(Continued)

*Primary Examiner* — Kathleen Mosser
(74) *Attorney, Agent, or Firm* — Roger D. Emerson, Esq.; Ray C. Meiers, Esq.; Emerson Thomson Bennett LLC

(57) ABSTRACT

A cap composition that can mechanically attach to a stethoscope headpiece, the cap composition having a cap; a cap element having a design that includes a shape and characteristic dimensions that enable the cap to mechanically attach to a stethoscope headpiece; and a speaker attached to and positioned on or at least partially within the cap, such that when the cap is attached to the stethoscope headpiece, the speaker is either touching or proximate to the stethoscope diaphragm such that a sound or signal emitted by the speaker can cause the stethoscope diaphragm to vibrate.

15 Claims, 8 Drawing Sheets

FOREIGN PATENT DOCUMENTS

| | | |
|---|---|---|
| JP | 2005-077521 | 3/2005 |
| JP | 2005-227534 | 8/2005 |
| KR | 10-2006-0025301 A | 3/2006 |
| WO | WO2006/047400 | 5/2006 |

OTHER PUBLICATIONS

International Search Report, dated Jul. 14, 2009, Korean Intellectual Property Office, PCT/US2008/082417.

* cited by examiner

AUSCULTATION TRAINING DEVICE AND RELATED METHODS

This application is a continuation-in-part of, and claims priority to U.S. patent application Ser. No. 11/935,468 filed on Nov. 16, 2007 and now pending, and claims priority to U.S. Provisional Patent Application Ser. No. 61/023,971 filed on Jan. 28, 2008 now pending, both of which are incorporated herein by reference in their entirety.

BACKGROUND OF THE INVENTION

1. Field of Invention

Embodiments are directed to devices, methods, and systems relating to auscultation training.

2. Description of the Related Art

Auscultation is the act of listening to sounds within the body as a method of diagnosis. A stethoscope is an example of an auscultation device that is used in the medical field to listen to internal sounds in the human body, such as for example heart sounds, breathing (breath sounds), intestinal noises, and blood flow in arteries and veins. Acoustic stethoscopes operate on the transmission of sound from a headpiece, via air-filled hollow tubes, to a listener's ears. The headpiece may include a diaphragm that can be placed against a human body for sensing sound. Body sounds vibrate the diaphragm, creating acoustic pressure waves that travel through the tubing to the listener's ears.

Using a stethoscope or other auscultation device to diagnose a patient requires training in detecting and identifying abnormal sounds. Standardized patients are a valuable training tool in medical education and have been extensively researched. Though standardized patients give students one-on-one interaction with real human subjects, most standardized patients do not present abnormal symptoms. As a result, simulators and mannequins are often used to train or test students on auscultation devices, such as stethoscopes. Auscultation training mannequins may include a sound generating device embedded within the body of the mannequin to produce sounds consistent with an abnormal physical condition, which students must detect and identify.

BRIEF SUMMARY OF THE INVENTION

Some embodiments relate to an auscultation training device, comprising: a medical training mannequin including a means for detecting the position of an auscultation device relative to the mannequin; a controller in electronic communication with the means for detecting relative position and the controller is adapted to receive location data from the means for detecting relative position, wherein the data indicates the position of the auscultation training device relative to the medical training mannequin; a database of auscultation training sound data in electronic communication with the controller, wherein the controller is adapted to select and retrieve auscultation sound data corresponding to data received from the means for detecting relative position; a sound generating device in electronic data communication with the database and adapted to convert sound files communicated therefrom into acoustic wave signals; and an auscultation device having at least one ear piece in acoustic communication with the sound generating device and adapted to transmit acoustic wave signals to a human ear.

Other embodiments relate to a process for auscultation training, comprising the steps of: simulating a patient; detecting the position of an auscultation device relative to the simulated patient; selecting an auscultation sound data file from a database, wherein the selected sound corresponds to the detected relative position of the auscultation device; and communicating the auscultation sound data file to at least one sound generating device disposed in or on at least one auscultation device.

Still other embodiments relate to an auscultation training device, comprising: an inanimate means for simulating a patient; a means for detecting the relative position of an auscultation device; a means for storing prerecorded auscultation sound data files; a means for selecting one or more prerecorded sound data files from the means for storing; a means for audibly delivering the one or more sound files to at least one ear piece adapted to fit a human ear; and a means for controlling the means for containing, the means for selecting, and the means for delivering.

Further aspects and concepts will become apparent to those skilled in the art after considering the following description and appended claims in conjunction with the accompanying drawings.

DETAILED DESCRIPTION OF THE INVENTION

Figure 1:
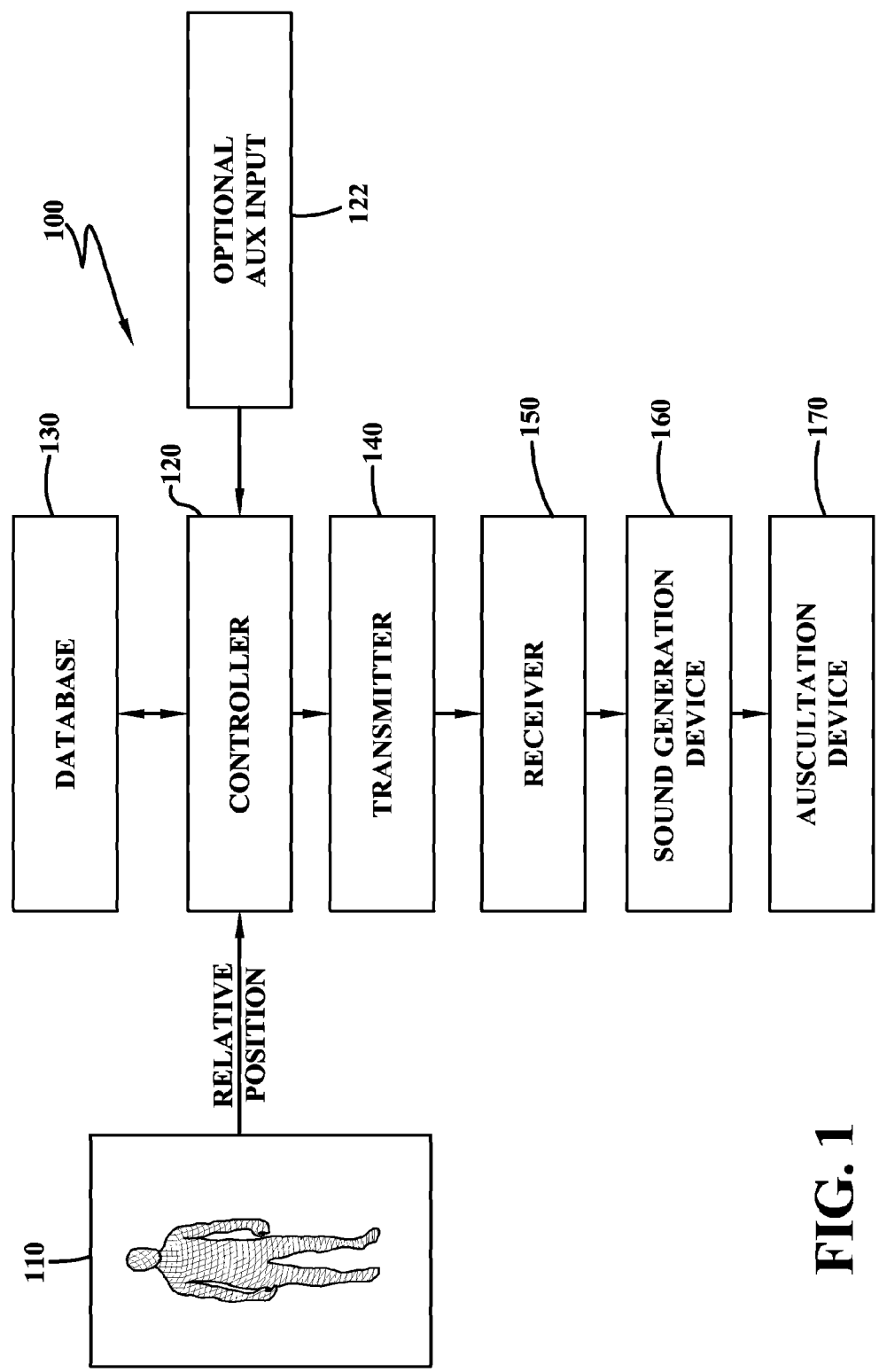
FIG. 1 is a connectivity chart showing the flow of information through an embodiment.

The present invention generally relates to systems for auscultation training and methods associated with such systems. Some embodiments include a database of pre-recorded sounds, a means for selecting one or more prerecorded sounds from the database, and a means for audibly delivering the one or more sounds to a trainee. Furthermore, some embodiments include one or more controller units to control the selection and/or delivery of sounds.

Some embodiments include a mock auscultation device adapted to present selected sounds to a trainee. In other embodiments, a real auscultation device is fitted or retrofitted with a means for presenting selected sounds to a trainee. Real and mock auscultation devices can include, without limitation, stethoscopes and are collectively referred to herein as "auscultation devices." Other auscultation devices can also be appropriate depending upon the nature of the intended use. For instance, a mock or real stethoscope can be appropriate for training medical students to make diagnoses based on body sounds. However, a stethoscope may not be appropriate for training an engineer or technician to recognize diagnostic sounds emanating from a machine. One of ordinary skill in the art will readily recognize the appropriate form that the real or mock auscultation device should take according to the intended use. The following disclosure uses stethoscopes as an exemplary auscultation device; however, the present invention is not limited to such devices.

Some embodiments comprise a system including a medical training mannequin, and at least one auscultation device. Such embodiments include a means for detecting the relative position of an auscultation device in relation to the mannequin and relay its relative position to a controller device. The controller device is adapted to select sound data from the database that corresponds to the detected location and retrieve, or cause the retrieval of, the sound data from the database. According to some embodiments, the controller also communicates the sound data to a transmitter, or causes the sound data to be so communicated. The sound data can then be communicated by the transmitter to at least one receiver that is disposed on or in the at least one auscultation device, such as a stethoscope. The receiver can also be in electronic communication with a sound-generating device adapted to convert electronic signals from the receiver into acoustic wave signals. Such acoustic wave signals can then be audibly communicated to an ear piece and to a human ear.

Each of the foregoing components can be in communication with one or more of the other components by any appropriate means including wireless and hardwired electronic connections. Furthermore, each component can be physically disposed in an on-board relation to any other component or can be in a remote physical relation to any other component. For example, in some embodiments all of the foregoing components are contained in a single physical unit. In other embodiments each of the foregoing components is remote relative to each of the other foregoing components. Still other embodiments are somewhere between these extremes, wherein some components are grouped together into physical units and others are remote from each other. A wide variety of relations can be appropriate depending on the specific application, and one of skill in the art will be able to select a desired relation without undue experimentation.

Any of a wide variety of wireless communications means can be appropriate for data and/or control signal transmission. For instance, some appropriate means can include radio or infrared communications means. More specifically, some appropriate protocols include, without limitation WiFi, Bluetooth® (Bluetooth is a registered certification mark of Bluetooth Sig Inc., Bellevue, Wash.), ZigBee® (ZigBee is a registered trademark of ZigBee Alliance Corp., San Ramon, Calif.) and the like. Similarly, any of a wide range of hardwired connections can be appropriate. Some such connections include, without limitation, serial bus, parallel bus, SCSI, I2C (inter-integrated circuit), SPI (serial peripheral interface), and the like or any combination thereof. One of skill in the art will recognize that a wide range of wireless and hardwire technologies are available, and will be able to select an appropriate technology without undue experimentation.

In some embodiments the mannequin is fitted with a means for detecting the relative position of an auscultation device. Such embodiments are capable of determining the region of the mannequin to which a trainee is applying the auscultation device. For example, some embodiments can localize the auscultation device in a heart region, a lung region, any of a variety of visceral or thoracic regions, and the like.

According to some embodiments the means for detecting relative position can comprise one or more proximity switches or one or more arrays thereof. In such embodiments, the proximity switches, or arrays thereof, are adapted to detect the position of an auscultation device, such as a metallic stethoscope head, relative to the mannequin. The position data can then be communicated to a controller unit.

Alternatively, other embodiments are adapted to triangulate the position of the auscultation device. According to such embodiments, the auscultation device is fitted with a transmitter beacon for broadcasting a predetermined signal. The mannequin includes two or more receivers adapted to receive the transmitter's beacon signal, and data obtained from the receivers can be analyzed according to known algorithms to calculate the position of the auscultation device relative to the mannequin. The present invention is not limited to the use of triangulation or proximity switches. Alternative devices can be used to determine the relative position of an auscultation device, and one of skill in the art will be able to select an appropriate device without undue experimentation.

In some embodiments the controller can be in hardwired electronic communication with the means for detecting the relative position of an auscultation device. For example, in some embodiments the controller can be disposed on or in the mannequin and may be linked to the means for detecting relative position by at least one hardwired electrical connection. In other embodiments, the controller may be hardwired, but also disposed apart from the mannequin, for example, in a desktop or handheld module. In still other embodiments, the controller can be in wireless communication with the means for detecting relative position.

Some embodiments also include a database. Suitable databases can comprise any appropriate data structure such as, without limitation, lists, hash tables, or hierarchical, relational, or network models. In some embodiments the database simply comprises a group of sound files stored together on, for instance, a CD-ROM or flash memory. The database can be stored on any appropriate machine memory means including, without limitations, volatile or nonvolatile memories, EPROMs, EEPROMs, magnetic media such as tapes or hard drives, optical media such as CD-ROMs, and the like or any combination thereof. Furthermore, the database can be physically disposed in any of a variety of locations. For example, in some embodiments the database may be an on-board component of the mannequin. In other embodiments, the database may be a disposed apart from the mannequin and may be a component of the controller unit, or a component of a module hardwired thereto. In still other embodiments the database may be physically disposed in a standalone, desktop or handheld means, or even as a component of the auscultation device.

Sounds can be selected in and retrieved from the database by one or more of a variety of means. In some embodiments a sound is automatically selected according to the detected position of the auscultation device. For instance, if the system determines that the auscultation device is positioned over the heart region of the mannequin, then a heart sound is selected.

Alternatively, sound data may be selected and retrieved from the database according to a computer program. For instance, a program may select a particular sound based on several factors including the detected position of the auscultation device, the condition of the simulated patient (e.g. is the simulated patient experiencing a myocardial infarction), and the status of other simulator components (e.g. have chest compressions, defibrillation, or a simulated drug injection been detected). Additionally, some programs may include a weighted randomness factor, wherein the system selects a sound according to several factors, but also includes a degree of randomness in its selection.

Still further, in other embodiments a sound may be selected by a human operator. For instance, in one example an instructor or other person may use a remote handheld push-button unit to select an auscultation sound for presentation to the trainee.

Some embodiments also include a transmitter suitable for transmitting auscultation sound data. The transmitter can be physically disposed in any of a variety of locations depending upon the specific application. For instance, the transmitter may be an on-board component of the mannequin, the controller, the database or any combination thereof. Accordingly, suitable transmitters can receive auscultation sound data though hardwire connections or wirelessly depending upon the specific architecture adopted. In one embodiment, the controller receives data indicating the position of an auscultation device relative to the mannequin, selects and retrieves a corresponding sound file from the database and communicates the sound file through a hardware connection to the transmitter, which then wirelessly transmits the sound file. One of skill in the art will recognize that this is only one of many possible architectures.

Some embodiments also include a receiver adapted to receive signals broadcast by the transmitter. The receiver can be disposed in any appropriate location on or in the auscultation device. For instance, in one embodiment the receiver can be disposed in the head piece of a stethoscope. The receiver can be adapted to convert a signal received from the transmitter into an electrical signal and communicate the signal to a sound generation device such as, without limitation, a speaker. Typically, the receiver is hardwired to the sound generation device; however, this is not required. In one example, the receiver and speaker are disposed in the head piece of a stethoscope. Therefore, the auscultation sound signal is converted into an acoustic wave within the head piece and audibly communicated to a listener's ears in the same way that the stethoscope normally transmits auscultation sounds.

Additionally, some embodiments can include a plurality of auscultation devices each having a receiver. For instance, it may be desirable to have a first auscultation device for a student and a second auscultation device for an instructor, so that the student and instructor can both listen to the same auscultation sound. Furthermore, it may be desirable to have an auscultation device for each of a plurality of students and for one or more instructors. Accordingly, an entire class can listen to the same auscultation sound simultaneously through their own devices. This may be especially beneficial, for instance, when an instructor is teaching a class the meaning of a particular sound.

Turning now to the figures, FIG. 1 is a connectivity diagram showing how information generally flows through the embodiment 100. The embodiment 100 includes a mannequin 110 fitted with a means for detecting the relative position of an auscultation device 170. The mannequin 110 communicates position data to controller 120. Controller 120 determines the position of the auscultation device 170 relative to mannequin 110, and thus determines which sound, or class of sounds, is appropriate for transmission. For instance, if the auscultation device is found to be proximal to a heart region, then an appropriate sound may be one or more heart sounds. Accordingly, controller 120 selects an appropriate sound file from database 130 and retrieves the selected sound file. The controller 120 then communicates the sound file to a transmitter 140, which wirelessly broadcasts the sound file according to a predetermined protocol. The broadcast signal is received by receiver 150 and communicated to a sound generation device 160, such as a speaker. The sound generation device 160 communicates an acoustic wave through an auscultation device 170, which audibly delivers the acoustic wave to a listener.

Alternatively, controller 120 can receive input from an auxiliary input source 122, such as a pushbutton, a keypad, or other human interface means. Accordingly, some embodiments enable a person, such as an instructor, to select auscultation sounds to be presented to the trainee. Thus, in some embodiments the means for detecting the relative position of the auscultation device can be overridden or even absent entirely.

Figure 2:
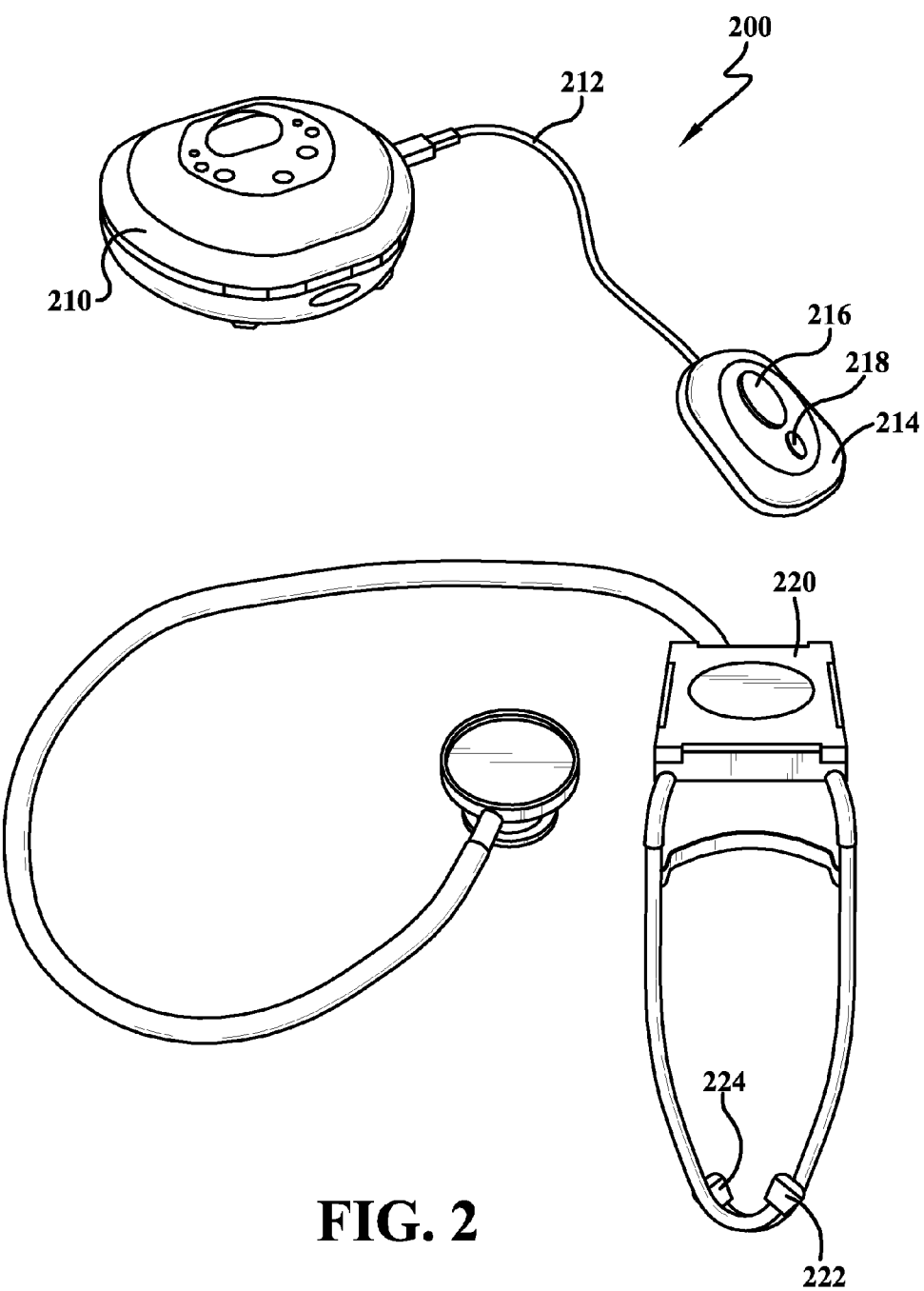
FIG. 2 is a pictorial diagram of an embodiment.

FIG. 2 is a drawing of an embodiment comprising a CD-ROM player 210. The player 210 is hardwired through connection 212 to a handheld controller device 214 comprising a sound selector. According to this example, the CD-ROM player receives push button commands from the controller 214. For example, a user would press button 216 to cursor through a list of sounds and would push button 218 to select the desired sound. The selected sound would then be broadcast by CD-ROM player 210 using an appropriate transmitter (not shown). The auscultation device 220 receives the broadcast signal using an appropriate receiver (not shown) and converts the signal into an acoustic wave. The acoustic wave can then be communicated through the auscultation device and audibly delivered to a listener through ear pieces 222, 224.

Figure 2A:
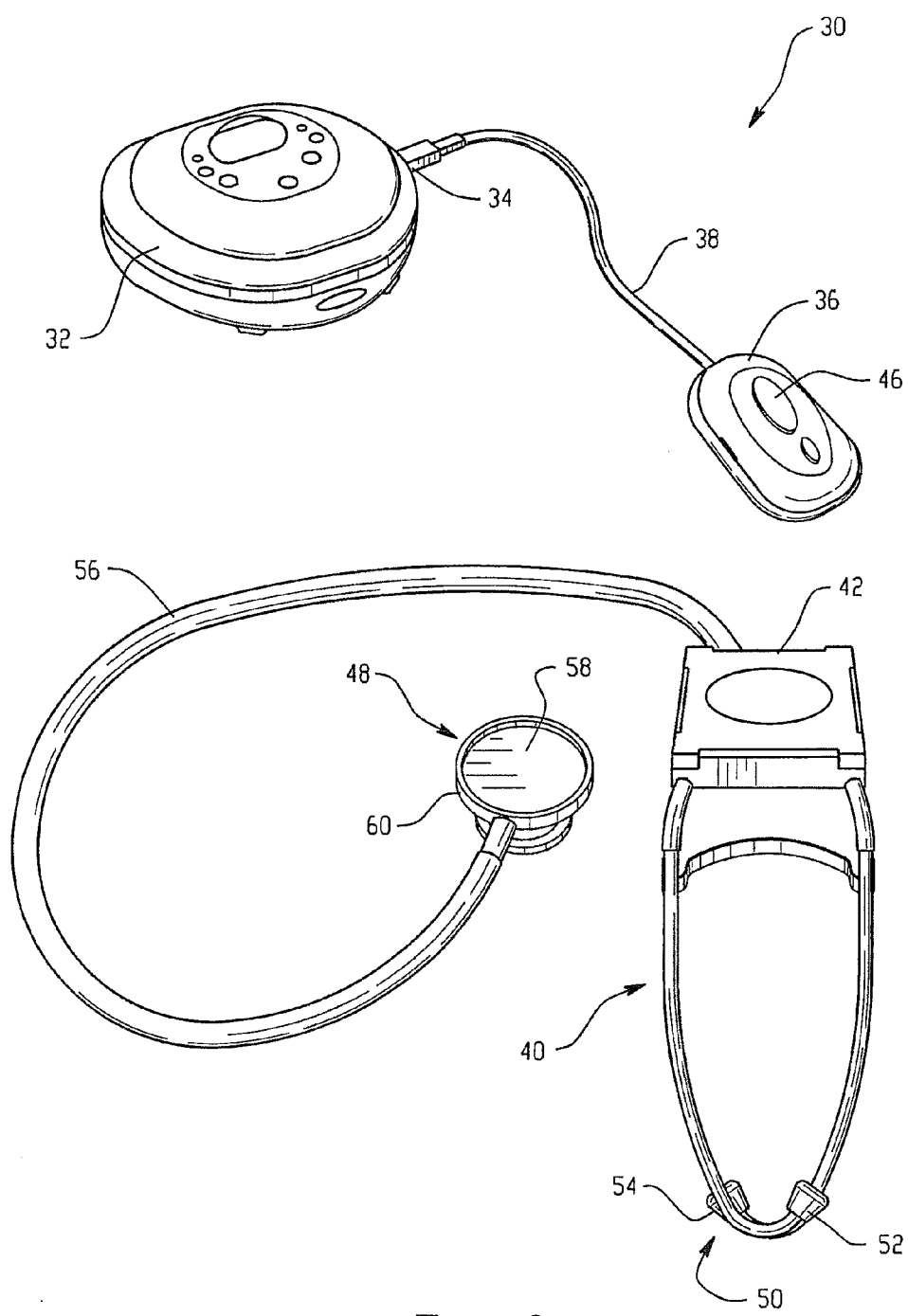
FIG. 2A is a pictorial diagram of another embodiment.

FIG. 2A illustrates an embodiment of an exemplary arrangement for auscultation training. Arrangement 30 includes audio device 32 that is a species of device 200 described in relation to FIG. 2. Audio device 32 may include output 34, such as a headphone output jack, and FM radio transmitter 36 may attach to audio device 32 via wire 38 that plugs into output 34. FIG. 2A's embodiment includes auscultation device 40 realized as a stethoscope and FM radio receiver 42 and speaker 350 (see FIG. 3) mounted to stethoscope 40.

Stethoscope 40 is illustrated as an acoustic stethoscope but may be any suitable stethoscope, including all electronic stethoscopes. Stethoscope 40 includes headpiece 48, which may be a headpiece assembly, earpiece assembly 50, which may include at least one piece, e.g., a pair of earpieces 52, 54, and tubing 56, which may be a tubing assembly, having a generally hollow interior. Tubing assembly 56 connects earpiece assembly 50 to headpiece assembly 48. Headpiece assembly 48 may include diaphragm 58 and body portion 60.

Figure 3:
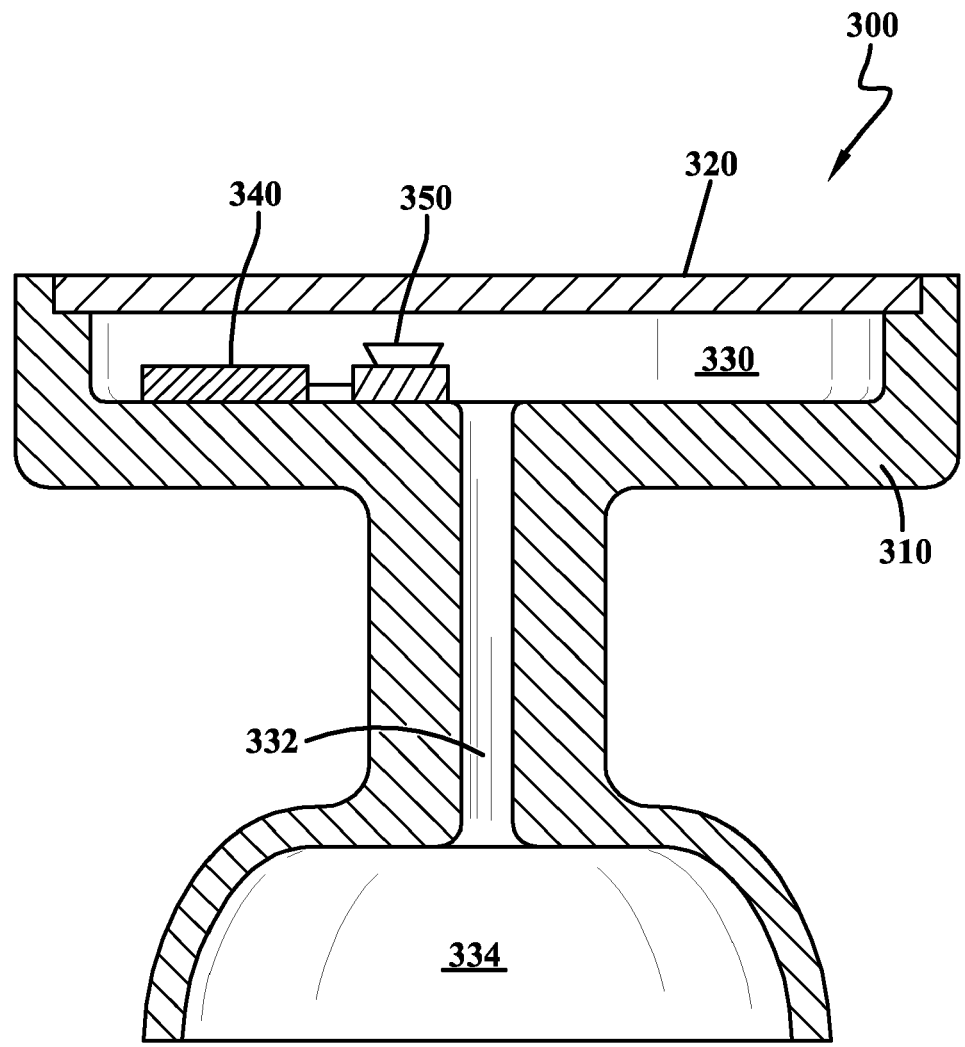
FIG. 3 is a diagram on a head piece of an embodiment.

FIG. 3 is a drawing of an embodiment comprising a head piece of a stethoscope 300. According to the example in FIG. 3, the head piece 300 comprises a body 310 defining a first cavity 330, and a channel 332 in acoustic communication with a second cavity 334. Thus, the first 330 and second 334 cavities are in acoustic communication. The head piece 300 also includes a diaphragm 320. When the auscultation device is used to detect acoustic waves external to the head piece 300, the diaphragm 320 vibrates in resonance with such sounds and generates a duplicate acoustic wave inside the head piece 300, which can be audibly delivered to a listener. However, when the auscultation device is used to listen to sounds transmitted according to the present invention, a sound data signal is received by receiver 340, which is disposed in the first cavity 330 and is mounted on an inner surface of the body 310. The receiver then communicates the received signal to a speaker 350, which generates a corresponding acoustic wave. The acoustic wave is then communicated through the first cavity 330 to the second cavity 334 through the channel 332 and can then be audibly delivered to a listener. The sound generating device 350 can be at least partially directed at the diaphragm 320. In the exemplary embodiment, as shown in FIG. 3, the sound generating device 350 is positioned to emit sound waves directly at the diaphragm 320.

Figure 4:
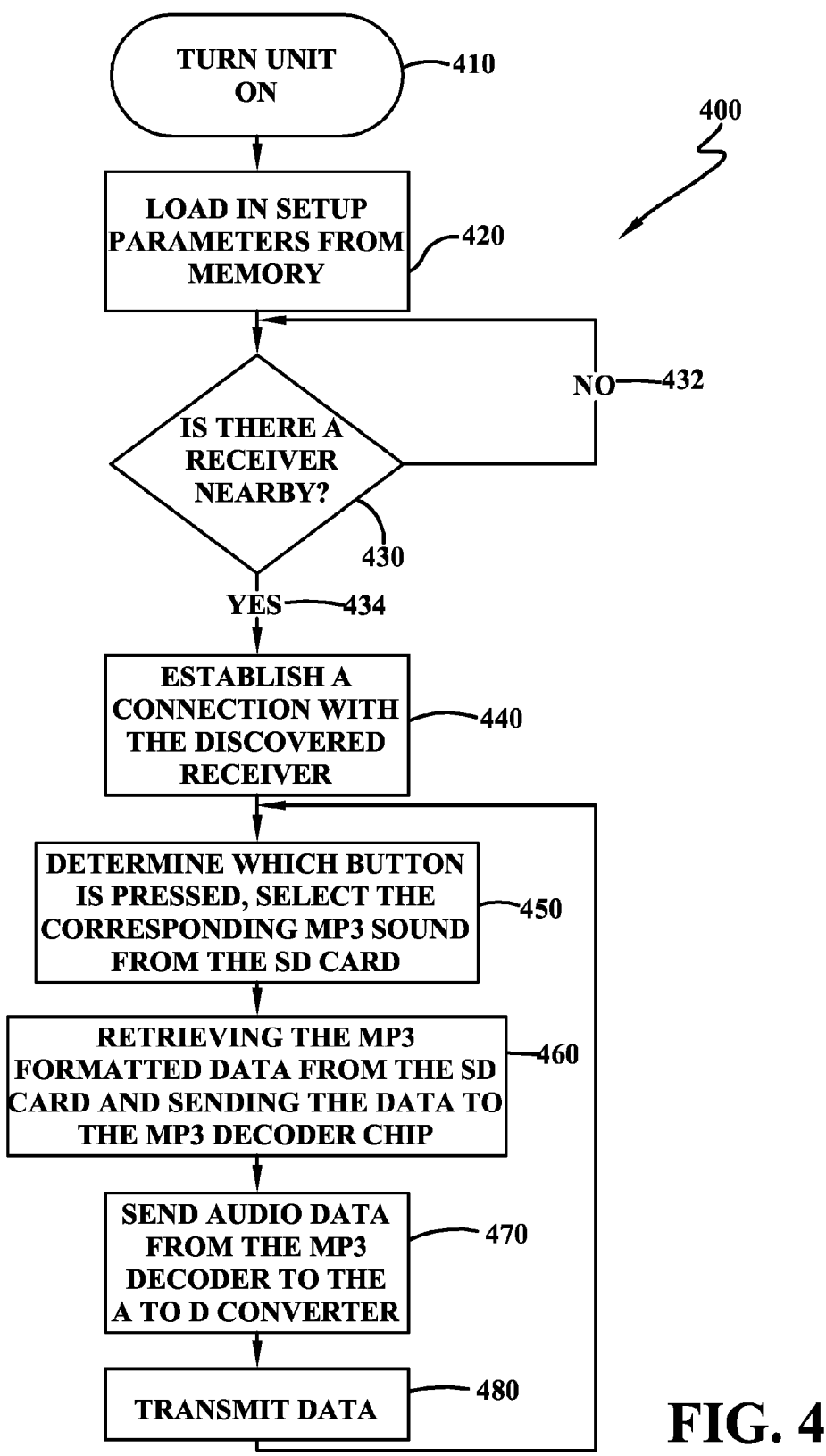
FIG. 4 is a flowchart illustrating the operation of a transmitter embodiment.

FIG. 4 is a flowchart of a process embodiment 400. According to the embodiment 400 a process for operating a transmitter comprises a first step of turning the unit on 410. Another step comprises loading setup parameters in memory 420. The embodiment 400 also includes checking for a receiver within range of the transmitter 430. According to this embodiment, if a receiver is not found the embodiment continues to check 432 for a receiver until one is found or until the process is otherwise terminated such as by disengaging the power, or by issuing a timeout or termination command. When a receiver is found, the process continues 434 to a next step. According to this embodiment the next step comprises establishing a communications connection between the transmitter and receiver 440. According to this process embodiment 400 the device for carrying out the process comprises a plurality of buttons, each button being associated with a predetermined sound file. After establishing a connection with the receiver an operator can select and push a button to transmit a corresponding sound to the receiver. In this case the sound file comprises an MP3 format. Accordingly, a next step in the process embodiment 400 comprises detecting that a button has been pushed, determining which button, and selecting the corresponding sound file from a memory device 450. A next step includes retrieving the corresponding sound file and sending the file to an MP3 decoder chip 460. The output of the decoder chip can then be directed to an analog to digital converter 470. The digitized sound file can then be transmitted by the transmitter to the receiver 480. According to this embodiment 400, the steps from 450 to 480 can repeat as needed for each communication session between a transmitter and receiver.

Figure 5:
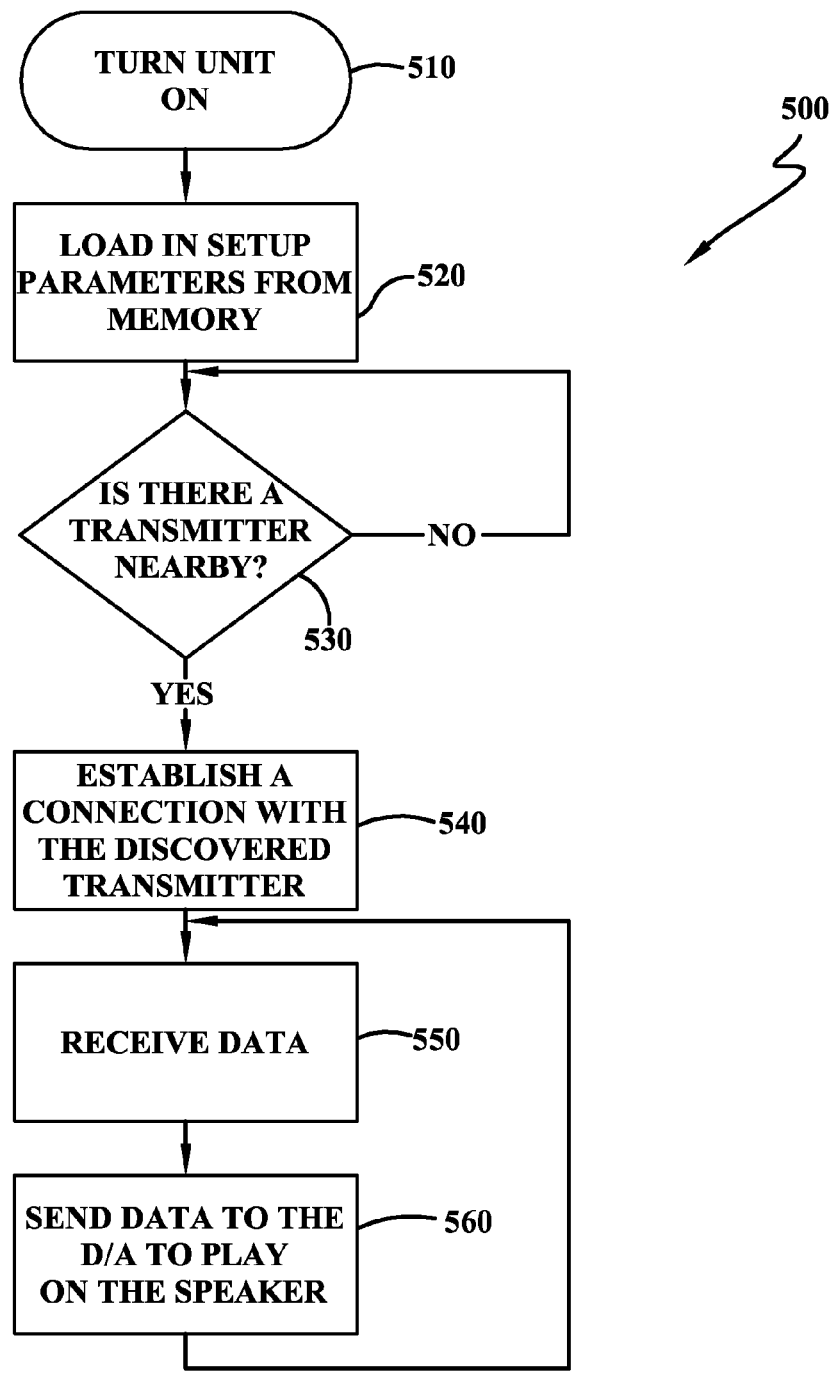
FIG. 5 is a flowchart showing the operation of a receiver embodiment in connection with an audible simulation.

FIG. 5 is a flowchart of a receiver process embodiment 500 of the present invention. According to the embodiment in FIG. 5 a first step in a process for operating a receiver of the present invention includes turning on 510 the receiver unit. A second step includes loading 520 setup parameters in memory. A next step includes determining 530 whether there is a transmitter within range of the receiver. According to the embodiment 500 shown in FIG. 5 if no transmitter is detected, the receiver continues attempting to find a transmitter until one is found, or until the process is otherwise terminated such as by turning off power to the unit, or issuing a timeout or termination command. Assuming a transmitter is found in step 540, the next step is establishing 540 a communications connection between the transmitter and receiver. After establishing a connection, a next step according to embodiment 500 is receiving 550 data from the transmitter. According to process embodiment 500 data received from the transmitter can be routed 560 to a digital-to-analog converter. The output of the converter can be directed to a speaker to produce an audible sound corresponding to the MP3 file from which it originated.

Figure 6:
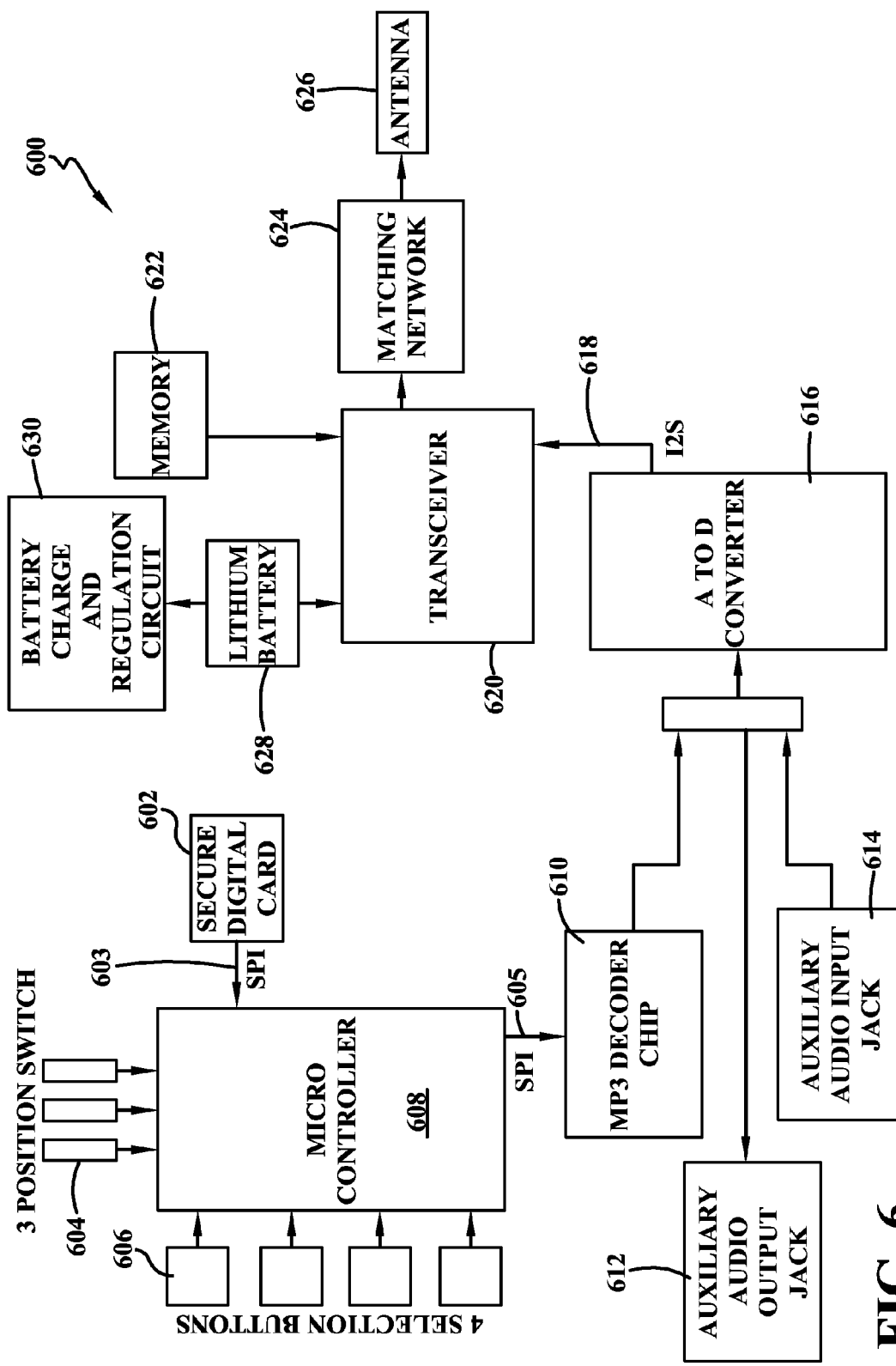
FIG. 6 is a schematic diagram of a transmitter circuit embodiment.

FIG. 6 is a block diagram of a transmitter embodiment 600. According to this embodiment a Secure Digital card 602, i.e. SD card, is adapted to contain electronic data comprising one or more audio files, such as an MP3 file. The card can be removably inserted into an onboard SD card reader. The SD card reader is in electronic communication with a microcontroller 608 through a SPI serial bus 603. The microcontroller 608 is also in electronic communication with a three position switch 604, which is adapted to select a set of one or more sounds. Additionally, the microcontroller 608 is also in electronic communication with a set of four selection buttons 606, which are adapted to select audio files contained on the SD card 602. Thus, when an operator pushes one of the set of four buttons it causes a predetermined audio file to be read and directed to MP3 decoder chip 610 through SPI serial bus 605. The analog output of the MP3 decoder chip 610 is directed to analog-to-digital converter 616, which accepts it as input and directs the resulting digital output to transceiver 620 through 12S serial bus 618. Transceiver 620 is also in bidirectional electronic communication with memory 622. Accordingly, transceiver 620 is adapted to transfer data to and from memory 622. Additionally, according to FIG. 6, transceiver 620 in electrical communication with a lithium battery 628, which provides transceiver 620 with a power source. Furthermore, lithium battery 628 electrically interfaces with transceiver 620 through battery charge and regulation circuit 630 which is adapted to extract electrical power from battery 628 and provide it to transceiver 620 according to predetermined criteria. According to some embodiments regulation circuit 630 is also adapted to regulate battery recharging processes. Finally, transceiver 620 is in electronic communication with a matching network 624, which is adapted to match the transceiver's 620 output impedance with the input impedance of a receiver. Matching network 624 then communicates the electronic signal to broadcasting antenna 626, which is adapted to broadcast the MP3 audio file.

According to FIG. 6 embodiment 600 also includes auxiliary audio output jack 612, which is adapted to receive signals from MP3 decoder chip 610 and direct such signals, or a portion thereof, to an external circuit. Further according to FIG. 6, embodiment 600 includes auxiliary audio input jack 614. Therefore, embodiment 600 is adapted to receive audio data from sources other than an SD card, and in formats other than MP3. In some embodiments plugging an audio source into audio input jack 614 causes the MP3 layer to be disconnected, and only the audio streaming from jack 614 is transmitted.

Figure 7:
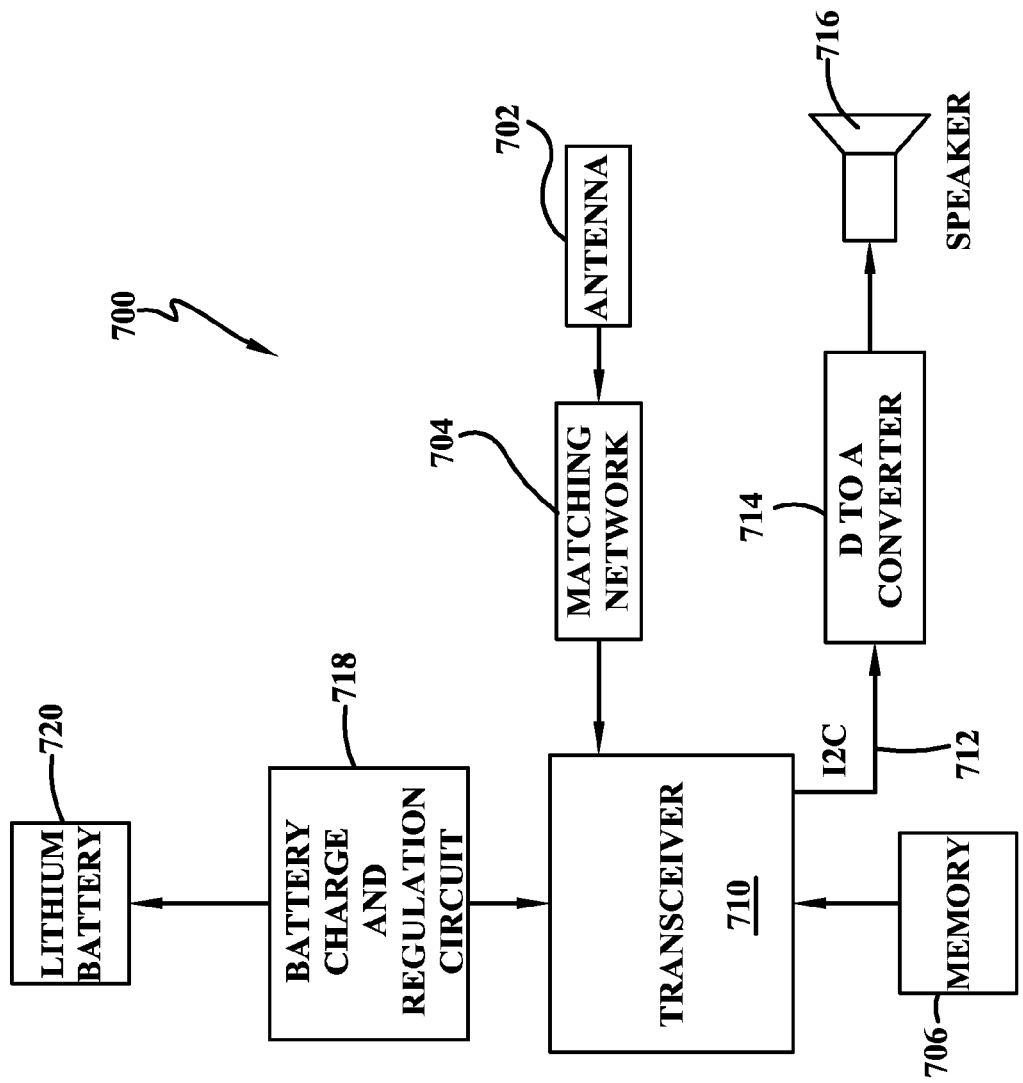
FIG. 7 is a schematic diagram of a receiver circuit embodiment.

FIG. 7 is a block diagram of a receiver embodiment 700. Receiver 700 includes a receiving antenna 702, which is in electronic communication with matching network 704. Matching network 704 is adapted to match the impedance of receiver 700 to the impedance of transmitter 600. Matching network 704 is also in electronic communication with transceiver 710 and is adapted to communicate received signals to transceiver 710. The output of transceiver 710 can be communicated to speaker 716 through digital-to-analog converter 714. Transceiver 710 is also in bidirectional communication with memory 706. Accordingly, transceiver 710 can upload data to memory 706 and/or download data from memory 706 and direct the data to speaker 716. In some embodiments memory 706 is adapted to function as a buffer memory. Transceiver 710 is in electrical communication with lithium battery 720, which provides transceiver 710 with electrical power for operation. Lithium battery 720 communicates electrical power to transceiver 710 through battery charge and regulation circuit 718. Battery charge and regulation circuit 718 is adapted to extract electrical power from battery 720 and provide it to transceiver 710 according to predetermined criteria. According to some embodiments battery charge and regulation circuit 718 is also adapted to regulate battery recharging processes.

The embodiments have been described, hereinabove. It will be apparent to those skilled in the art that the above methods and apparatuses may incorporate changes and modifications without departing from the general scope of this invention. It is intended to include all such modifications and alterations insofar as they come within the scope of the appended claims or the equivalents thereof.

I claim:
1. An auscultation training device comprising:
an auscultation device having at least one ear piece, a headpiece defining a first cavity, a diaphragm at least partially enclosing said first cavity, wherein said at least on ear piece and said first cavity are in acoustic communication such that sound waves are communicated from said first cavity to said ear piece;
a medical training mannequin including a means for detecting a position of said auscultation device relative to said medical training mannequin and emitting a location data signal corresponding to the relative position;

a controller in electronic communication with said means for detecting the position to receive the location data signal;
a database of auscultation training sound data in electronic communication with said controller, wherein said controller is operable to select and retrieve auscultation training sound data corresponding to the location data signal;
a transmitter in electronic data communication with said database to receive and transmit the auscultation training sound data;
at least one receiver operable to receive the auscultation training sound data from said transmitter; and
a sound generating device in electronic data communication with said at least one receiver and operable to convert
the auscultation training sound data into sound waves, wherein said sound generation device is disposed in said first cavity of said headpiece proximate to said diaphragm.

2. The auscultation training device of claim 1 wherein at least one of said controller, said database, and said transmitter is integrated with respect to said medical training mannequin.

3. The auscultation training device of claim 1 wherein said transmitter and said receiver in electronic communication with one another through a hardwire connection or a wireless connection.

4. The auscultation training device of claim 3 wherein said hardwire connection is a serial bus, parallel bus, SCSI, I2C, or SPI.

5. The auscultation training device of claim 3 wherein said wireless connection is a wireless local area network, a wireless personal area network, or a low-rate wireless personal area network.

6. The auscultation training device of claim 1 wherein said means for detecting the position comprises at least one array of proximity switches.

7. The auscultation training device of claim 1 wherein said database is written to a computer readable medium comprising a flash memory, EPROM, EEPROM, CD-ROM, magnetic tape, or hard drive.

8. The auscultation training device of claim 1 wherein said database comprises a list, a hash table, a hierarchical database, a relational database, or a network database.

9. The auscultation training device of claim 1 wherein said database is read using an MP3 player, a compact disk player, a personal computer, or a flash drive.

10. The auscultation training device of claim 1 wherein said transmitter is adapted to transmit signals selected from one or more of radio, FM radio, AM radio, or infrared.

11. The auscultation training device of claim 1 wherein said auscultation device functions as both an acoustic stethoscope receiving sound waves external to the first cavity generated by a human body and channel the sound waves to the at least one ear piece and also as a training device receiving sound waves in said first cavity generated by said sound generating device.

12. The auscultation training device of claim 1 wherein said sound generating device is at least partially directed at said diaphragm.

13. The auscultation training device of claim 1 wherein said sound generating device is positioned to emit sound waves directly at said diaphragm.

14. An auscultation training device comprising:
an auscultation device having at least one ear piece, a headpiece defining a first cavity, a diaphragm at least partially enclosing said first cavity, wherein said at least on ear piece and said first cavity are in acoustic communication such that sound waves are communicated from said first cavity to said ear piece;
a medical training mannequin including a means for detecting a position of said auscultation device relative to said medical training mannequin and emitting a location data signal corresponding to the relative position;
a controller in electronic communication with said means for detecting the position and operable to receive the location data signal;
a database of auscultation training sound data in electronic communication with said controller, wherein the controller is operable to select and retrieve auscultation training sound data corresponding to the location data signal;
a transmitter in electronic data communication with said database and operable to receive and transmit the auscultation training sound data;
at least one receiver operable to receive the auscultation training sound data from said transmitter;
a sound generating device in electronic data communication with said at least one receiver and operable to convert the auscultation training sound data into sound waves, wherein said sound generation device is disposed in acoustic communication with said at least one ear piece; and
wherein said controller is adapted to receive command signals from a human operator such that said command signals overrides the location data signal in the selection of the auscultation training sound data.

15. An auscultation training device comprising:
a plurality of auscultation devices each having at least one ear piece, a headpiece defining a first cavity, a diaphragm at least partially enclosing said first cavity, wherein said at least on ear piece and said first cavity are in acoustic communication such that sound waves are communicated from said first cavity to said ear piece;
a medical training mannequin including a means for detecting a position of said auscultation device relative to said medical training mannequin and emitting a location data signal corresponding to the relative position;
a controller in electronic communication with said means for detecting the position and operable to receive the location data signal;
a database of auscultation training sound data in electronic communication with said controller, wherein the controller is operable to select and retrieve auscultation training sound data corresponding to the location data signal;
a transmitter in electronic data communication with said database and operable to receive and transmit the auscultation training sound data;
a plurality of receivers each operable to receive the auscultation training sound data from said transmitter and each disposed in a different one of said plurality of auscultation devices;
a plurality of sound generating devices each in electronic data communication with one of said plurality of receivers and each operable to convert the auscultation training sound data into sound waves, wherein each of said plurality of sound generation devices is disposed in acoustic communication with an ear piece of one of said plurality of auscultation devices.

* * * * *